US00PP09834P

United States Patent [19]

Lyrene

[11] Patent Number: Plant 9,834

[45] Date of Patent: Mar. 25, 1997

[54] BLUEBERRY PLANT CALLED 'SOUTHMOON'

[76] Inventor: Paul Lyrene, 1143 Fifield Hall Horticultural Sciences Dept., Univ. of FL, Gainesville, Fla. 32611

[21] Appl. No.: 527,753

[22] Filed: Sep. 11, 1995

[51] Int. Cl.[6] ..... A01H 5/00

[52] U.S. Cl. ..... Plt./33.1

[58] Field of Search ..... Plt./33.1

[56] References Cited

PUBLICATIONS

Galletta, Gene J., "Blueberries and Cranberries" *Advances in Fruit Breeding* 1775 Purdue Research Foundation, West Lafayette, Ind. pp. 154–185.

*Primary Examiner*—James R. Feyrer

[57] ABSTRACT

A new and distinct low-chill, tetraploid highbush blueberry (Vaccinium) variety of complex ancestory, based largely on *V. corymbosum* L. with some genes from *V. darrowi* Camp, *V. ashei* Reade, and *V. angustifolium* Ait. Its novelty consists of the following unique combination of features:

1. The ability to flower and leaf vigorously in an area where the mean temperature of the coldest month is 58 degrees F.
2. The ability to retain dormancy during warm periods in January and February.
3. The ability to produce ripe fruit 70 days after flowering in north-central Florida.
4. The ability to ripen 80% of its crop between May 1 and Jun. 1 in north-central Florida.
5. Produces fruit that is large and firm with good flavor and firmness, and a small pedicel scar.
6. Produces a vigorous, upright-growing plant with tolerance to *Phytophthora cinnamoni* and *Botryosphaeria dothedia.*
7. Can readily be propagated from softwood cuttings.

1 Drawing Sheet

ORIGIN OF THE VARIETY

'Southmoon' originated as a seedling in 1981. The seed lot from which it was grown was produced by compositing the seeds produced when four tetraploid, low-chill highbush blueberry selections from the Florida breeding program ('Sharpblue', 'Flordablue', 'Avonblue' and FL4-76) were hand pollinated in a greenhouse with pollen from another Florida highbush selection, FL80-46. FL80-46 was an F-1 hybrid between FL73-8 (an improved highbush selection from the Florida breeding program), and a wild tetraploid *V. corymbosum* clone selected from the forests of Alachua County, FLA. as a source of high vigor, disease resistance, and adaptation to the southern climate. Because the wild parent has small, dark fruit, the clone to which it was crossed to produce FL80-46 and the clones to which FL80-46 was crossed to obtain southmoon, were chosen for large fruit size and high fruit quality. All crosses were made in the blueberry breeding greenhouse at the University of Florida. None of the plants involved was patented. 'Southmoon' was selected as a superior seedling in a high-density fruiting nursery in Gainesville, Fla. in 1985, and was given the test number FL85-15. The plant was propagated by softwood cuttings, and a test plot of 15 ramets was established at Gainesville in January, 1987. Other test plots were later established at several sites in north Florida using rooted cuttings. Observations over 10 years have indicated that 'Southmoon' has characteristics that would make it a useful cultivar.

ASEXUAL PROPAGATION OF THE VARIETY

The new and distinct variety has been propagated by softwood cuttings on numerous occasions. In every case, all the ramets have displayed the varietal characteristics without exception.

SUMMARY OF THE VARIETY

'Southmoon' is vigorous and produces an upright plant with a low chill requirement. Although its chromosome number has not been determined cytologically, both its pedigree and its crossing behavior the mean January temperature is 56F. with an average of about 400 hours per winter duration of temperatures below 45F. Because of its low chilling requirement and early flowering time, crop losses due to March and early-April freezes could be excessive when 'Southmoon' is grown in the southeastern United states north of a line from Savannah, Ga. to Shreveport, La. The plants have moderate to high tolerance to the two most serious diseases of highbush blueberries in the southeastern United States, Phytophthora root rot and Botryosphaeria stem blight. The mean date of 50% anthesis at Gainesville is February 27 (range February 10 to March 12 over 8 years of record). The mean date of mid-harvest averages May 9 at Gainesville (range of May 3 to May 17 over 6 years of record). Berries are large (average 2.3 grams per berry) and dark blue in color. The small dry pedicel scar and high firmness give the berries a long post-harvest life. Both flavor and texture were rated high in organoleptic tests. The plant roots readily from softwood cuttings under mist.

DESCRIPTION OF THE VARIETY

Figure 1:
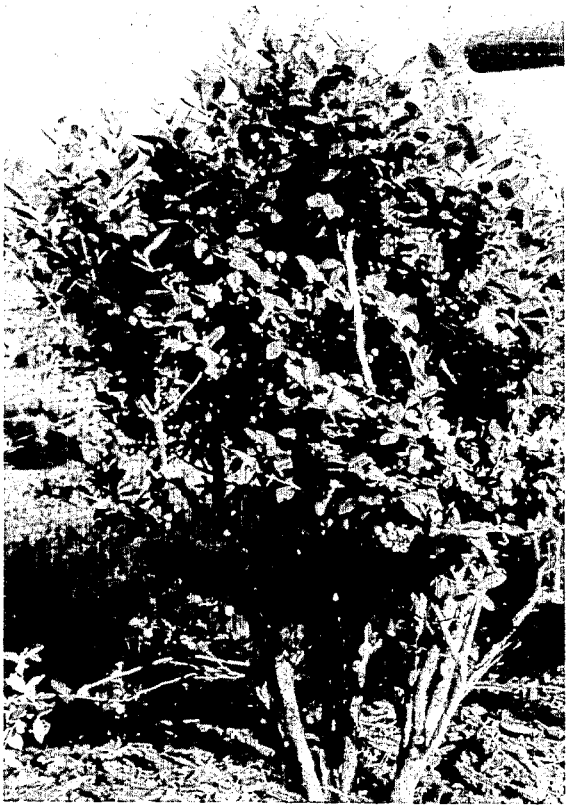
FIG. 1 illustrates an 8 year old specimen of the plant of 'Southmoon' in side elevation and shows the multiple trunk and branch scaffolding and also depicts the canopy and fruit clusters of the plant at a seasonal stage when half the fruit have been harvested in late May in central Florida.
Figure 2:
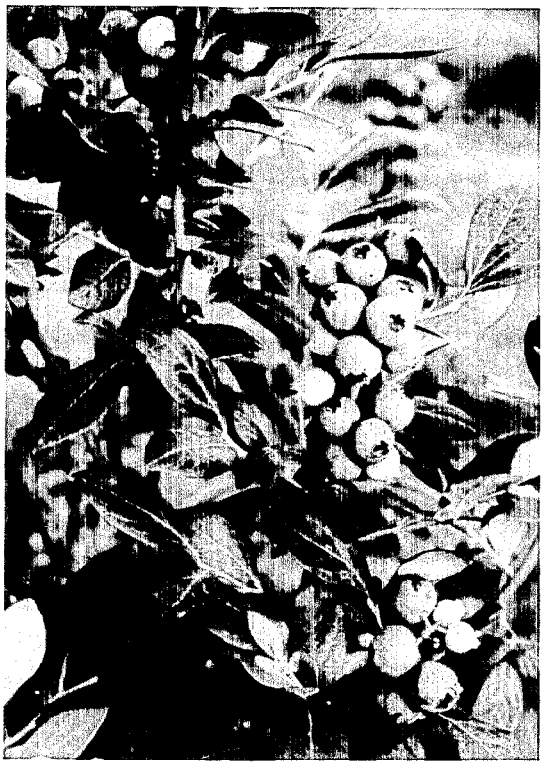
FIG. 2 shows, in larger scale, fruit clusters of 'Southmoon' as well as the top and bottom surfaces of foliage along with the character and color of wood of fruiting age.
Figure 3:
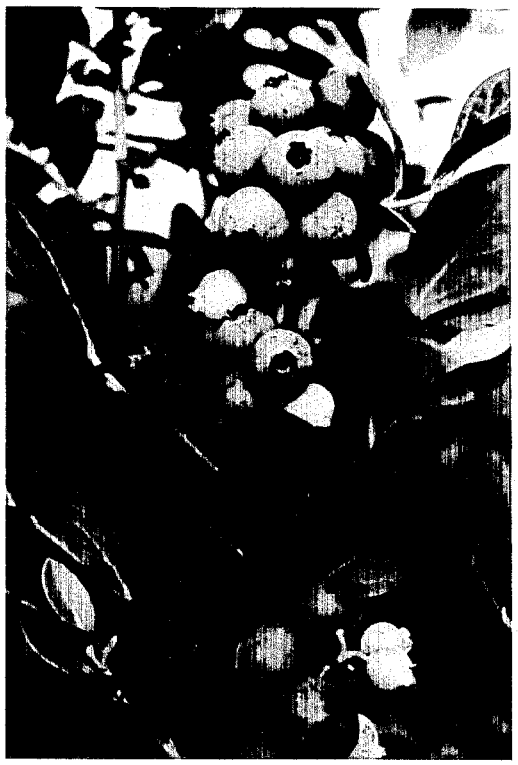
FIG. 3 depicts typical fruit clusters in even closer scale; shown are the fruit indicate that it is tetraploid (2n=4x=48). 'Southmoon' has been crossed on numerous occasions with other tetraploid cultivars, and the number of viable seedlings produced per pollinated flower has been high, whether it was used as the pollen or the seed parent. 'Southmoon' breaks both leaf and flower bud without delay, even after abnormally mild winters in Gainesville, Fla., where shape, fruit blossom end characteristics, fruit color and fruit surface bloom; with some of the fruit depicted being ready for harvest as well as immature fruit within the cluster, and further depicts the top and bottom surfaces of mature and new foliage of the plant.

The following is a detailed botanical description of the new and distinct variety of blueberry, its flowers, fruit and foliage, based on observations of specimens grown in Gainesville, Fla. Color descriptions, except those given in common terms, use terminology from "The Pantone Book of Color" 1990, by Leatrice Eiseman and Lawrence Herbert, Harry N. Abrams, Inc. Publishers, New York.

Bush:

*Size.*—Large; on good soil, plants reach 2 m tall with a canopy diameter of 130 cm within 6 years in north Florida. Rooted cuttings 12 cm tall transplanted to a field nursery on Sep. 25 averaged 80 cm tall the following July.

*Vigor.*—High.

*Growth habit.*—Upright.

*Productivity.*—High.

*Flower bud production.*—Moderately heavy.

Trunk:

*Suckering tendency.*—Below-average tendency to sprout new shoots from rhizomes. However, it does produce enough basal shoots to renew the bush. After several years of fruiting, plants require annual, post-harvest, summer pruning to maintain production of strong flowering wood.

*Texture.*—Bark on older trunks rough, but exfoliates to smooth,

*Color.*—Two-year old wood "Gravel" (PANTONE 14-1014).

Twigs:

*Color.*—Current-season twigs in August "Hay" (PANTONE 15-0636).

*Internode length.*—Averaged 1.43 cm on upright, regrowth shoots measured in July following hard January pruning.

Leaves:

*size.*—Medium. Average length 55 mm. Average width 25 mm.

*Shape.*—Ovate, apically acute.

*Margin.*—Entire.

*Color of upper surface.*—Green olive (PANTONE 17-0535).

*Color of lower surface.*—Beechnut (PANTONE 14-0425).

Pubescence, upper surface.—Glabrous except numerous short, white hairs on midrib visible at 30×.

*Pubescence, lower surface.*—A few stalked glands on midrib visible at 30×. Scattered pubescence on midrib and larger veins. Otherwise glabrous.

*Pubescence, leaf margins.*—Glands spaced along the margins of the petiolar half of the blade.

Flowers:

*Size.*—Medium.

*Color.*—White.

*Shape.*—Urceolate.

*Pollen production.*—Copious.

*Flowering period.*—Early: 50% anthesis averages February 27.

*Inflorescence morphology.*—Pedicel length medium and peduncle internode length medium, leading to a moderately loose fruit cluster.

*Self compatibility.*—Partially self compatible but must be cross-pollinated with another tetraploid cultivar for full productivity.

Berry:

*Size.*—Large, about 2.3 grams per berry

*Shape.*—Somewhat flattened; First-ripe berries 11 mm tall and 15 mm diameter.

*Color.*—Cadet (PANTONE 18-3812).

*Pedicel scar.*—Small and dry.

*Firmness.*—Very firm.

*Flavor.*—Sweet with slight acidity.

*Calyx lobes.*—Small, irregular.

*Calyx tube aperture.*—Small diameter.

*Texture.*—Good: small seeds, thin skins, few sclerids.

*Wax.*—Moderately persistent.

*Maturity date.*—Early-midseason: Mid-harvest averages May 9 at Gainesville.

*Clusters.*—Normally 4 to 8 berries per peduncle.

I claim:

1. A new and distinct highbush blueberry plant, substantially as illustrated and described, characterized by its low chilling requirement, large fruit, high fruit quality, early ripening, and resistance to Phytophthora root rot and Botryosphaeria stem blight, having the ability to be asexually propagated by softwood cuttings.

* * * * *